US006277988B1

(12) United States Patent
Campbell et al.

(10) Patent No.: US 6,277,988 B1
(45) Date of Patent: *Aug. 21, 2001

(54) SOLVENT-FREE METHOD FOR PREPARING STERICALLY HINDERED PHOSPHORAMIDATES

(75) Inventors: John Robert Campbell; James Anthony Cella; Gregory Ronald Gillette, all of Clifton Park, NY (US); John Edward Kochanowski, Great Barrington, MA (US); Matthew Ladd Reitz, Clifton Park, NY (US)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/515,801

(22) Filed: Feb. 29, 2000

Related U.S. Application Data

(60) Provisional application No. 60/151,193, filed on Aug. 27, 1999, and provisional application No. 60/164,909, filed on Nov. 11, 1999.

(51) Int. Cl.$^7$ ............... C07F 9/6509; C07F 9/24
(52) U.S. Cl. ............ 544/337; 558/138; 558/157
(58) Field of Search ............. 544/337; 558/138, 558/157

(56) References Cited

U.S. PATENT DOCUMENTS

| 2,385,713 | 9/1945 | Kosolapoff | 260/461 |
|---|---|---|---|
| 2,878,255 | 3/1959 | Toy et al. | 260/461 |
| 3,868,376 | 2/1975 | Hotten . | |
| 4,196,090 | 4/1980 | Lilburn | 252/49.9 |

FOREIGN PATENT DOCUMENTS

| 2 307 519 | 2/1973 | (DE) . |
| 7-70158 | 3/1995 | (JP) . |
| 10175985 | 6/1998 | (JP) . |
| WO 00/12612 | 3/2000 | (WO) . |

OTHER PUBLICATIONS

John J. Talley, "Preparation of Sterically Hindered Phosphoramidates", J. Chem. Engr. Data, vol. 33, pp. 221–222, 1988.

European Search Report for PCTR International Application No. PCT/US 00/20639.

*Primary Examiner*—Deborah C. Lambkin
*Assistant Examiner*—Andrea M. D'Souza
(74) *Attorney, Agent, or Firm*—S. Bruce Brown; Noreen C. Johnson

(57) ABSTRACT

Sterically hindered phosphoramidates such as N,N'-bis[di-(2,6-xylenoxy)phosphinyl]piperazine are prepared by the reaction of a sterically hindered diaryl chlorophosphate, such as di-(2,6-xylyl) chlorophosphate, with a basic nitrogen compound containing at least two basic N—H groups, preferably a heterocyclic compound such as piperazine, in a predominantly liquid, solvent-free reaction mixture. The reaction may be conducted in the melt or in the presence of a non-solvent carrier, typically an aliphatic hydrocarbon. An excess of the basic nitrogen compound is employed as an acid acceptor.

23 Claims, No Drawings

SOLVENT-FREE METHOD FOR PREPARING STERICALLY HINDERED PHOSPHORAMIDATES

CROSS-REFERENCE TO RELATED APPLICATIONS

This application claims priority from provisional applications Serial Nos. 60/151,193 filed Aug. 27, 1999 and 60/164,909, Nov. 11, 1999 which are incorporated herein by reference.

BACKGROUND OF THE INVENTION

This invention relates to the preparation of phosphoramidates, and more particularly to their preparation from nitrogen bases and diaryl chlorophosphates.

The use of sterically hindered phosphoramidates such as N,N'-bis[di-(2,6-xylenoxy)phosphinyl]piperazine (hereinafter sometimes "XPP") as flame retardant additives for synthetic resins, especially thermoplastic resins such as polycarbonates, ABS resins and blends thereof, has been discovered to have particular advantages including improved high temperature stability of the resulting blends. Reference is made, for example, to U.S. Pat. No. 5,973,041 and to copending, commonly owned applications Ser. Nos. 09/235,679 and 09/364,915.

XPP and analogous compounds may be conveniently prepared by the reaction of a diaryl chlorophosphate, such as di-(2,6-xylyl) chlorophosphate, with a heterocyclic compound containing two basic N—H groups, such as piperazine. According to the prior art as illustrated by Talley, *J. Chem. Eng. Data*, 33, 221–222 (1983), this reaction may be conducted in chloroform as solvent, in the presence of triethylamine as an acid acceptor. The triethylamine is employed in stoichiometric amount or in excess, and reacts with the by-product hydrogen chloride to drive the reaction to completion.

The Talley paper describes the preparation of a number of analogous compounds including those derived from such nitrogen compounds as benzylamine, cyclohexylamine, aniline, ethylenediamine and p-phenylenediamine as well as piperazine. Reported yields were as high as 90% for the reaction with aniline, and as low as 61% for the reaction with p-phenylenediamine. Piperazine afforded XPP in a yield of only 68%, one of the lowest reported.

If the use of XPP as a flame retardant additive is to be commercially feasible, it is necessary to improve its yield by a significant amount. Also, it is desirable to minimize use on a commercial scale of the relatively toxic solvent chloroform, as well as other solvents which can add complexity to the reaction by reason of the need for isolation of product from the solvent, as well as disposal or recycle of solvent and of extraneous acid acceptors such as triethylamine.

It is of interest, therefore, to develop high-yield methods for the preparation of XPP and analogous compounds with a minimum of unit operations.

SUMMARY OF THE INVENTION

The present invention is based on the discovery that the preparation of sterically hindered phosphoramidates in high yield from sterically hindered diaryl chlorophosphate and nitrogen bases may be carried out in a solvent-free reaction mixture. In addition, said reaction may also be performed in a solvent-free reaction mixture in the presence of at least one liquid carrier which is a non-solvent for the product.

Accordingly, in one embodiment the invention is a method for preparing a sterically hindered phosphoramidate which comprises contacting a sterically hindered diaryl chlorophosphate with a basic nitrogen compound containing at least two basic N—H groups in a predominantly liquid, solvent-free reaction mixture, said basic nitrogen compound being employed in an amount effective to react with both said diaryl chlorophosphate and by-product hydrogen chloride.

In another embodiment the invention is a method for preparing a phosphoramidate which comprises contacting a diaryl chlorophosphate with a basic nitrogen compound containing at least two basic N—H groups in a predominantly liquid, solvent-free reaction mixture, said basic nitrogen compound being employed in an amount effective to react with both said diaryl chlorophosphate and by-product hydrogen chloride, said phosphoramidate having a glass transition temperature of at least about 0° C., preferably of at least about 10° C., and most preferably of at least about 20° C.

DETAILED DESCRIPTION; PREFERRED EMBODIMENTS

Within the context of the present invention a sterically hindered phosphoramidate is one in which at least one aryl substituent linked to heteroatom-phosphorus has at least one substituent on the aryl ring ortho to the aryl-heteroatom-phosphorus linkage. The sterically hindered diaryl chlorophosphates employed in the method of this invention include those having the formula

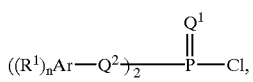

(I)

wherein Ar is an aromatic group, each $R^1$ is independently alkyl, aryl or halo, $Q^1$ is oxygen or sulfur, $Q^2$ is oxygen, sulfur, or $NR^1$, and n has the value of 1 up to the number of free valency sites on the aromatic ring or rings, and at least one $R^1$ substituent on the aryl ring is ortho to the heteroatom-phosphorus linkage. Preferably, Ar is a phenyl ring and n has the value of 1–5. Preferably, each $R^1$ is $C_{1-4}$ primary or secondary alkyl; most preferably, methyl, and n is 2 with each substituent ortho to the heteroatom-phosphorus linkage. Thus, preferred chlorophosphates are di-(2,4,6-trimethylphenyl) chlorophosphate and di-(2,6-dimethylphenyl) chlorophosphate, also known as di-(2,6-xylyl) chlorophosphate.

Any compound, acyclic or cyclic, containing at least two basic N—H groups may be employed. Suitable compounds include those of the formula

(II)

wherein each $R^2$ is a $C_{1-4}$ primary or secondary alkyl radical or both $R^2$ radicals taken together are ethylene. Illustrative acyclic compounds are N,N'-dimethylethylenediamine and N,N'-diethylethylenediamine. Heterocyclic compounds are generally preferred; they are illustrated by piperazine and 1,2,3,4-tetrahydroquinoxaline, both unsubstituted and substituted. Piperazine is most preferred.

In a preferred embodiment, the method of the invention may be used to produce a phosphoramidate having a glass transition temperature of at least about 0° C., preferably of at least about 10° C., and most preferably of at least about 20° C. In particular, the method of the invention may be used to produce a phosphoramidate of the formula III:

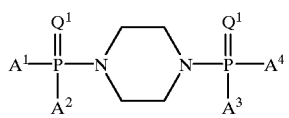
(III)

wherein each $Q^1$ is independently oxygen or sulfur; and each of $A^{1-4}$ is independently an alkyloxy, alkylthio, airyloxy, or arylthio residue, or an aryloxy or arylthio residue containing at least one alkyl or halogen substitution, or mixture thereof; or an amine residue. In an especially preferred embodiment of the invention, each $Q^1$ is oxygen, and each $A^{1-4}$ moiety is a 2,6-dimethylphenoxy moiety or a 2,4,6-trimethylphenoxy moiety. These phosphoramidates are piperazine-type phosphoramidates. In the above formula wherein each $Q^1$ is oxygen, and each $A^{1-4}$ moiety is a 2,6-dimethylphenoxy moiety, the glass transition temperature of the phosphoramidate is about 62° C. and the melting point is about 192° C.

In another preferred embodiment, the method of the invention may be used to produce a phosphoramidate having a glass transition temperature of at least about 0° C., preferably of at least about 10° C., and most preferably of at least about 20° C., of the formula IV:

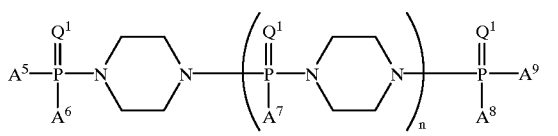
(IV)

wherein each $Q^1$ is independently oxygen or sulfur; and each of $A^{5-9}$ is independently an alkyloxy, alkylthio, aryloxy, or arylthio residue, or an aryloxy or arylthio residue containing at least one alkyl or halogen substitution, or mixture thereof; or an amine residue; and n is from 0 to about 5. In a more preferred embodiment, each $Q^1$ is oxygen, and each $A^{5-9}$ moiety is independently phenoxy, 2,6-dimethylphenoxy, or 2,4,6-trimethylphenoxy, and n is from 0 to about 5.

In another embodiment the method of the invention may be used to produce a phosphoramidate having a glass transition temperature of at least about 0° C., preferably of at least about 10° C., and most preferably of at least about 20° C., of the formula V:

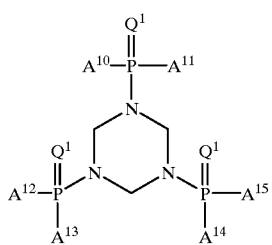
(V)

wherein each $Q^1$ is independently oxygen or sulfur; and each of $A^{10-15}$ is independently an alkyloxy, alkylthio, aryloxy, or arylthio residue, or an aryloxy or arylthio residue containing at least one alkyl or halogen substitution, or mixture thereof; or an amine residue. In a more preferred embodiment, each $Q^1$ is oxygen, and each $A^{10-15}$ moiety is independently phenoxy, 2,6-dimethylphenoxy, or 2,4,6-trimethylphenoxy.

In another embodiment the method of the invention may be used to produce a phosphoramidate having a glass transition temperature of at least about 0° C., preferably of at least about 10° C., and most preferably of at least about 20° C., of the formula VI:

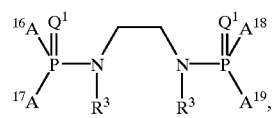
(VI)

wherein each $Q^1$ is independently oxygen or sulfur; each of $A^{16-19}$ is independently an alkyloxy, alkylthio, aryloxy, or arylthio residue, or an aryloxy or arylthio residue containing at least one alkyl or halogen substitution, or mixture thereof; or an amine residue; and each $R^3$ is an alkyl radical, or both $R^3$ radicals taken together are an alkylidene or alkyl-substituted alkylidene radical. In a preferred embodiment, each $Q^1$ is oxygen; both $R^3$ radicals taken together are an unsubstituted $(CH_2)_m$ alkylidene radical, wherein m is 2 to 10; and each $A^{16-19}$ moiety is independently phenoxy, 2,6-dimethylphenoxy, or 2,4,6-trimethylphenoxy. In a more preferred embodiment, each $Q^1$ is oxygen; each $R^3$ is methyl; and each $A^{16-19}$ moiety is independently phenoxy, 2,6-dimethylphenoxy, or 2,4,6trimethylphenoxy.

In another embodiment the method of the invention may be used to produce a phosphoramidate having a glass transition point of at least about 0° C., preferably of at least about 10° C., and most preferably of at least about 20° C., of the formula VII:

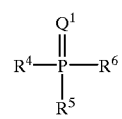
(VII)

wherein $Q^1$ is oxygen or sulfur, and $R^4$ is of the formula VIII:

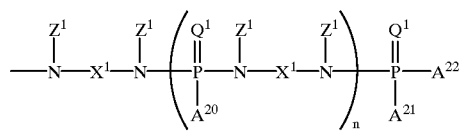
(VIII)

wherein each $Q^1$ is independently oxygen or sulfur; each of $A^{20-22}$ is independently an alkyloxy, alkylthio, aryloxy, or arylthio residue, or an aryloxy or arylthio residue containing at least one alkyl or halogen substitution, or mixture thereof; or an amine residue; each $Z^1$ is an alkyl radical, aromatic radical, or aromatic radical containing at least one alkyl or halogen substitution or mixture thereof; each $X^1$ is an alkylidene radical, aromatic radical, or aromatic radical containing at least one alkyl or halogen substitution or mixture thereof; n is from 0 to about 5; and $R^5$ and $R^6$ are each independently an alkyloxy, alkylthio, aryloxy, or arylthio residue, or an aryloxy or arylthio residue containing at least one alkyl or halogen substitution, or mixture thereof; or an amine residue. In a preferred embodiment, each $Q^1$ is oxygen; each $A^{20-22}$ moiety is independently phenoxy, 2,6-dimethylphenoxy, or 2,4,6-trimethylphenoxy; each $Z^1$ is methyl or benzyl; each $X^1$ is an alkylidene radical containing 2–24 carbon atoms; n is from 0 to about 5; and $R^5$ and $R^6$ are each independently phenoxy, 2,6-dimethylphenoxy, or 2,4,6-trimethylphenoxy.

In another embodiment the method of the invention may be used to produce a phosphoramidate having a glass transition point of at least about 0° C., preferably of at least about 10° C., and most preferably of at least about 20° C., of the formula IX:

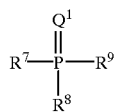

(IX)

wherein $Q^1$ is oxygen or sulfur; and $R^7$ is of the formula X:

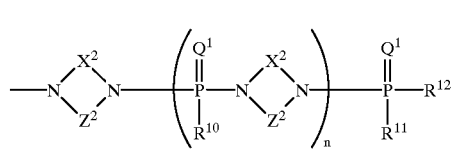

(X)

wherein each $Q^1$ is independently oxygen or sulfur; each $X^2$ is an alkylidene or alkyl-substituted alkylidene residue, aryl residue, or alkaryl residue; each $Z^2$ is an alkylidene or alkyl-substituted alkylidene residue; each of $R^{10}$, $R^{11}$, and $R^{12}$ is independently an alkyloxy, alkylthio, aryloxy, or arylthio residue, or an aryloxy or arylthio residue containing at least one alkyl or halogen substitution, or mixture thereof; or an amine residue; n is from 0 to about 5; and $R^8$ and $R^9$ are each independently an alkyloxy, alkylthio, aryloxy, or arylthio residue, or an aryloxy or arylthio residue containing at least one alkyl or halogen substitution, or mixture thereof; or an amine residue. In a preferred embodiment, each $Q^1$ is oxygen; each $X^2$ is an alkylidene or alkyl-substituted alkylidene residue; each $Z^2$ is an alkylidene or alkyl-substituted alkylidene residue; each of $R^8$, $R^9$, $R^{10}$, $R^{11}$, and $R_{12}$ is independently phenoxy, 2,6-dimethylphenoxy, or 2,4,6-trimethylphenoxy; and n is from 0 to about 5. In a more preferred embodiment, each $Q^1$ is oxygen; each $X^2$ and $Z^2$ is independently an unsubstituted alkylidene residue of the form $(CH_2)_m$, wherein m is 2 to 10; each of $R^8$, $R^9$, $R^{10}$, $R^{11}$, and $R^{12}$ is independently phenoxy, 2,6-dimethylphenoxy, or 2,4,6trimethylphenoxy; and n is from 0 to about 5. In an especially preferred embodiment, the phosphoramidate is derived from piperazine (i.e. $X^2$ and $Z^2$ are each $—CH_2—CH_2—$).

In another preferred embodiment, the method of the invention may be used to produce a cyclic phosphoramidate having a glass transition point of at least about 0° C., preferably of at least about 10° C., and most preferably of at least about 20° C. of the formula XI:

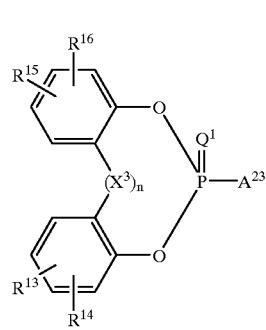

(XI)

wherein each of $R^{13-16}$ is independently a hydrogen or an alkyl radical, $X^3$ is an alkylidene radical, $Q^1$ is oxygen or sulfur, and $A^{23}$ is a group derived from a primary or secondary amine having the same or different radicals that can be aliphatic, alicyclic, aromatic, or alkaryl, or $A^{23}$ is a group derived from a heterocyclic arnine, or $A^{23}$ is a hydrazine compound. Preferably $Q^1$ is oxygen. It should be noted that when n is 0, then the two aryl rings are linked together at that site (i.e. where $X^3$ is absent) by a single bond in the positions ortho,ortho' to the phosphoryl bonds.

In another preferred embodiment, the method of the invention may be used to produce a bis(cyclic) phosphoramidate having a glass transition point of at least about 0° C., preferably of at least about 10° C., and most preferably of at least about 20° C. of the formula XII:

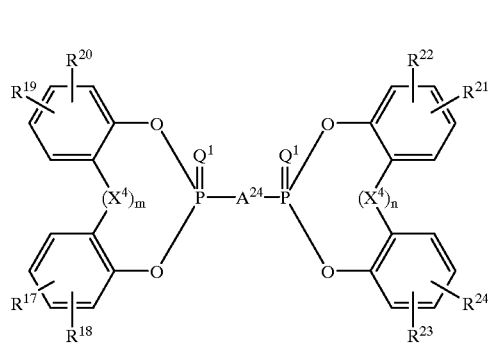

(XII)

wherein $Q^1$ is oxygen or sulfur, each of $R^{17-24}$ is independently a hydrogen or an alkyl radical; $X^4$ is an alkylidene radical; m and n are each independently 0 or 1; and $A^{24}$ is

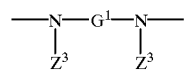

wherein $G^1$ is sulfur, an alkylidene radical, alkyl-substituted alkylidene radical, aryl radical, or alkatyl radical, and each $Z^3$ is independently an alkyl radical, an aryl radical, or an aryl radical containing at least one alkyl or halogen substitution, or mixture thereof; or wherein $A^{24}$ is

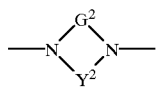

wherein $G^2$ is alkylidene, aryl, or alkaryl, and $Y^2$ is alkylidene or alkyl-substituted alkylidene. Preferred phosphoramidates are those wherein $Q^1$ is oxygen, $A^{24}$ is a residue of piperazine, and the phosphoramidate has a plane of symmetry through $A^{24}$. Highly preferred phosphoramidates include those wherein $Q^1$ is oxygen; $A^{24}$ is a residue of piperazine; the phosphoramidate has a plane of symmetry through $A^{24}$; at least one R substituent on each aryl ring is a methyl adjacent to the oxygen substituent; n and m are each 1; and $X^4$ is $CHR^{25}$ wherein $R^{21}$ is a hydrogen or an alkyl residue of from about 1 to about 6 carbon atoms. It should be noted that when either or both of m or n is 0, then the two aryl rings are linked together at that site (i.e. where $X^4$ is absent) by a single bond in the positions ortho, ortho' to the phosphoryl bonds.

The method may also be used to make phosphoramidates with intermediate glass transition temperatures by using a mixture of various substituted and non-substituted aryl moieties within the phosphoramidate.

According to the invention, the reaction between the diaryl chlorophosphate and the basic nitrogen compound is conducted in a predominantly liquid, solvent free reaction mixture. In one embodiment of the invention, said reaction is conducted in the melt. This embodiment typically requires a reaction temperature from the melting point of the reaction mixture up to about 250° C., preferably in the range of about 125–175° C. and most preferably about 140–160° C.

In another embodiment, the reaction mixture also contains at least one liquid carrier which is a non-s6solvent for the product. By "non-solvent for the product" is meant that under some conditions, at least, the product phosphoramidate precipitates from the liquid carrier. This may be because the product is not soluble therein under any conditions, or because it is not soluble therein at relatively low temperatures such as those in the range of about 20–50° C.

Suitable carriers include aliphatic hydrocarbons, especially $C_{5-16}$ aliphatic hydrocarbons which may be straight chain or branched, such as n-hexane, n-heptane, n-decane, n-dodecane and isooctane, and alicyclic hydrocarbons such as cyclopentane, cyclohexane and methylcyclohexane. Mixtures thereof may also be employed, as well as mixtures of such compounds with $C_{6-14}$ aromatic hydrocarbons such as toluene and xylene, provided said mixtures have the above-described properties qualifying them as non-solvents. n-Heptane is often particularly preferred. Reaction temperatures employed with a carrier liquid are typically in the range of about 90–150° C., preferably about 95–125° C.

It may, under certain conditions, be advantageous to incorporate in the reaction mixture a minor proportion of at least one aprotic nitrogen compound such as 4-dimethylaminopyridine, N-methylpyrrolidinone, dimethylformamide or dimethylacetamide. Such compounds can increase the reaction rate, particularly at relatively low temperatures. It is important, however, that they be present in proportions low enough to maintain the mixture solvent-free.

Another feature of the invention is the employment of the basic nitrogen compound in excess, whereupon it additionally serves as an acid acceptor. This affords significant advantages in such operations as recycle, since it is possible to recover piperazine hydrochlorides or the like and reconvert them to the recyclable basic nitrogen compound by simple treatment with base.

In another embodiment the method of the invention involves preparing a phosphoramidate through contacting a diaryl chlorophosphate with a basic nitrogen compound in a predominantly liquid, solvent-free reaction mixture under substantially water-free conditions. The substantial elimination of water leads to a significant reduction in the amount of pyrophosphate by-product. By "substantially water-free" is meant reaction conditions under which the ratio of equivalents of water to equivalents of chlorophosphate is less than about 0.05, preferably less than about 0.01, and more preferably less than about 0.005. Methods for minimizing water content are known to those with skill in the art and include drying the reaction apparatus, drying any non-solvent that may be present, and using reactants with minimal water content. Also, an inert atmosphere, such as nitrogen or argon, is preferably employed according to the invention.

Various methods of blending the reagents may be employed. For example, the diaryl chlorophosphate and basic nitrogen compound may simply be blended and heated to melt temperatures, or the basic nitrogen compound may be added, all at once or portionwise, to a mixture of the diaryl chlorophosphate and the carrier liquid.

Ratios of equivalents of basic nitrogen compound to diaryl chlorophosphate are generally in the range of about 0.9–6.0:1, preferably about 1.9–5.0:1, more preferably about 2.0–5.0:1, still more preferably about 2.0–3.0:1, yet more preferably about 2.0–2.5:1, and most preferably about 2.0–2.2:1. It is apparent that a 1:1 molar ratio will at least theoretically facilitate reaction on a stoichiometric level of a basic nitrogen compound containing two basic nitrogen atoms and therefore having an equivalent weight which is half its molecular weight, with both the diaryl chlorophosphate (equivalent weight equal to molecular weight) and by-product hydrogen chloride (wherein the ratio of equivalents is 2:1 basic nitrogen compound to chlorophosphate).

The progress of the reaction may be monitored by art-recognized analytical methods. In general, a reaction time on the order of 15–25 hours is adequate for the reaction to progress to effective completion. The phosphoramidate may then be isolated by conventional operations, typically including contact with aqueous mineral acid and, optionally, solvent, separation of the organic layer, washing and volatilization of solvent if necessary. If the reaction is conducted in the melt, such non-solvent isolation techniques as melt crystallization, sublimation, or zone refining may be employed. Employment of a non-solvent carrier liquid offers the advantage of facile separation of product from the reaction mixture by filtration or the like, followed by washing as necessary to produce the desired degree of purity.

The invention is illustrated by the following examples.

EXAMPLE 1

A vial was charged with 1 grams (g) (11.6 millimoles [mmol]) of piperazine and placed in an oil bath at 150° C. Di-(2,6-xylyl) chlorophosphate (3 g, 9.2 mmol) was added and the contents were heated and stirred for 18 hours. After several minutes, a liquid phase was formed which slowly turned solid. At the end of the reaction, a sample was analyzed by proton NMR and HPLC; it was found that conversion to XPP was greater than 95% and the yield greater than 93% of theoretical.

The remaining material was dissolved in 50 milliliters (ml) of chloroform and the solution was washed with dilute hydrochloric acid, water and then concentrated to a solid. Analysis showed that all excess piperazine and piperazine hydrochlorides had been removed. Subsequent recrystallization from methyl ethyl ketone afforded pure XPP having a melting point of 205° C.

EXAMPLE 2

A 250-ml flask was charged with 25 g (76.9 mmol) of di-(2,6-xylyl chlorophosphate and 50 ml of heptane and then charged with a nitrogen atmosphere. Anhydrous piperazine, 2.5 g, was added, followed by an additional 2.0 g 15 minutes later. The reaction mixture was stirred and heated to reflux. Rapid formation of solid was noted and HPLC analysis of a sample showed 54% conversion to XPP after 4 hours. Additional piperazine, 1.5 g (total 69.7 mmol), was added and the mixture was stirred and refluxed overnight. The next morning (22 hours total reaction time), copious solid had formed and the stirring had stopped. An additional 50 ml of heptane was added and HPLC of a sample showed 83% conversion. The suspension was filtered and suspended in boiling water for about one hour. HPLC analysis of the resulting solid material showed complete removal of unreacted di(2,6-xylyl chlorophosphate) and any trixylyl phosphate formed. The solid was suspended in methanol and refiltered. HPLC analysis of the resulting material showed complete removal of pyrophosphate impurity to provide excellent overall purity and recovery of XPP.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for preparing a sterically hindered phosphoramidate which comprises contacting a sterically hindered diaryl chlorophosphate with a basic nitrogen compound containing at least two basic N—H groups in a predominantly liquid, solvent-free reaction mixture, said basic nitrogen compound being employed in an amount effective to react with both said diaryl chlorophosphate and by-product hydrogen chloride.

2. A method according to claim 1 wherein the diaryl chlorophosphate has the formula

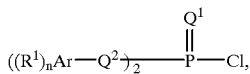

(I)

wherein Ar is an aromatic group, each $R^1$ is independently alkyl, aryl or halo, $Q^1$ is oxygen or sulfur, $Q^2$ is oxygen, sulfur, or $NR^1$, and n has the value of 1 up to the number of free valency sites on the aromatic ring or rings, and at least one $R^1$ substituent on the aryl ring is ortho to the heteroatom-phosphorus linkage.

3. A method according to claim 2 wherein Ar is phenyl, $Q^1$ and $Q^2$ are oxygen, n is 2 or 3, and each $R^1$ is methyl.

4. A method according to claim 1 wherein the basic nitrogen compound has the formula

wherein each $R^2$ is a $C_{1-4}$ primary or secondary alkyl radical or both $R^2$ radicals taken together are ethylene.

5. A method according to claim 4 wherein the basic nitrogen compound is heterocyclic.

6. A method according to claim 5 wherein the basic nitrogen compound is piperazine.

7. A method according to claim 1 wherein said contact is in the melt.

8. A method according to claim 7 wherein the contact temperature is in the range of about 125–175° C.

9. A method according to claim 8 wherein said contact is in the presence of at least one liquid carrier which is a non-solvent for the product.

10. A method according to claim 8 wherein the carrier is at least one aliphatic or alicyclic hydrocarbon or a mixture thereof with at least one aromatic hydrocarbon.

11. A method according to claim 10 wherein the carrier is a $C_{5-16}$ aliphatic hydrocarbon.

12. A method according to claim 11 wherein the carrier is n-heptane.

13. A method according to claim 10 wherein the contact temperature is in the range of about 90–150° C.

14. A method according to claim 13 wherein the ratio of equivalents of basic nitrogen compound to diaryl chlorophosphate is in the range of about 0.9–6.0:1.

15. A method according to claim 13 wherein the ratio of equivalents of basic nitrogen compound to diaryl chlorophosphate is in the range of about 2.0–3.0:1.

16. A method according to claim 1 wherein said contact is under substantially water-free conditions.

17. A method according to claim 7 wherein said contact is under substantially water-free conditions.

18. A method according to claim 9 wherein said contact is under substantially water-free conditions.

19. A method for preparing a phosphoramidate which comprises contacting a diaryl chlorophosphate with a basic nitrogen compound containing at least two basic N—H groups in a predominantly liquid, solvent-free reaction mixture, said basic nitrogen compound being employed in an amount effective to react with both said diaryl chlorophosphate and by-product hydrogen chloride, said phosphoramidate having a glass transition temperature of at least about 0° C.

20. The method of claim 18 in which the phosphoramidate has a glass transition temperature of at least about 10° C.

21. The method of claim 18 in which the phosphoramidate has a glass transition temperature of at least about 20° C.

22. A method for preparing N,N'-bis[di-(2,6-xylenoxy)phosphinyl]piperazine which comprises contacting di-(2,6-xylyl) chlorophosphate with piperazine in the melt, the molar ratio of said piperazine to said di-(2,6-xylyl) chlorophosphate being in the range of about 1.0–1.25:1.

23. A method for preparing N,N'-bis[di-(2,6-xylenoxy)phosphinyl]piperazine which comprises contacting di-(2,6-xylyl) chlorophosphate with piperazine in the presence of at least one $C_{5-16}$ aliphatic hydrocarbon as a liquid carrier, the molar ratio of said piperazine to said di-(2,6-xylyl) chlorophosphate being in the range of about 1.0–1.25:1.

* * * * *